United States Patent [19]

Wason

[11] 4,296,000

[45] Oct. 20, 1981

[54] ADSORBENTS FOR POLYOL PURIFICATION

[75] Inventor: Satish K. Wason, Churchville, Md.

[73] Assignee: J. M. Huber Corporation, Locust, N.J.

[21] Appl. No.: 172,335

[22] Filed: Jul. 25, 1980

Related U.S. Application Data

[63] Continuation-in-part of Ser. No. 74,226, Sep. 10, 1979, which is a continuation of Ser. No. 869,347, Jun. 13, 1978, abandoned.

[51] Int. Cl.$^3$ .................. B01J 20/10; B01J 20/08; B01J 20/04
[52] U.S. Cl. .................. 252/455 R; 252/449; 252/457; 423/334; 423/335
[58] Field of Search .......... 252/449, 451, 457, 455 R; 423/334, 335

[56] References Cited

U.S. PATENT DOCUMENTS

| 1,900,859 | 3/1933 | Connolly et al. | 423/335 |
| 2,355,388 | 8/1944 | Michael et al. | 252/457 X |
| 2,726,216 | 12/1955 | Kimberlin, Jr. | 423/335 X |
| 3,095,270 | 6/1963 | Kurach et al. | 423/334 X |
| 3,879,527 | 4/1975 | Bertorelli et al. | 423/334 X |
| 4,230,679 | 10/1980 | Mahler et al. | 252/451 X |

*Primary Examiner*—Carl F. Dees
*Attorney, Agent, or Firm*—Ernest A. Schaal; Harold H. Flanders

[57] ABSTRACT

A new silica is formed by hydrothermally reacting an aqueous dispersion of silica and sodium hydroxide, under certain conditions, to form a partly polymerized silicate; spray drying the mixture to form spheres of polysilicate; reacting the spray dried polysilicate with sulfuric acid to form a synthetic silica; and then filtering, washing and drying the silica. This and other silicas having a BET surface area greater than 60 sq m/g, and oil absorption of 60–140 cc/100 g, and with at least 70% of the silica larger than 44 microns are useful as adsorbents in polyol purification.

3 Claims, No Drawings

ADSORBENTS FOR POLYOL PURIFICATION

CROSS-REFERENCE TO RELATED APPLICATIONS

This is a continuation-in-part of application Ser. No. 74,226 filed Sept. 10, 1979 entitled SYNTHETIC SILICA AND USES THEREOF which is a continuation of application Ser. No. 869,347 filed June 13, 1978, now abandoned.

BACKGROUND OF THE INVENTION

This invention relates to a synthetic silica which is useful as an adsorbent for polyol purification.

Commercially available synthetic silicas are derived either by a liquid process or a vapor process. Products obtained by the vapor process are called fumed or pyrogenic silicas. Products obtained by the liquid process are either silica gels or precipitated silicas (silicon dioxides). Thus, there are three distinct types of synthetic silicas on the market.

1. PYROGENIC SILICAS

Pyrogenic or fumed silicas are prepared by reacting silicon tetrachloride vapor with oxygen and hydrogen gas at high temperatures. These products have high external surface areas.

2. SILICA GELS

Silica gels are of two types—hydrogels and aerogels. Hydrogels are prepared by reacting a soluble silicate, such as sodium silicate, with strong sulfuric acid. The gel is washed salt-free, dried, steam micronized, and then classified. Aerogels are prepared from crude hydrogels by displacing its water content with an alcohol. The alcohol is then recovered by heating the gel in an autoclave.

Aerogels are lighter and fluffier than hydrogels because the shrinkage of the gel structure is avoided during the drying process. Gels have very large surface areas, generally in the range of 300–1,000 sq m/g and high porosities.

3. PRECIPITATED SILICAS

Precipitated silicas are produced by the destabilization and precipitation of the silica from soluble sodium silicates by the addition of a mineral acid such as sulfuric acid or an acidic gas such as carbon dioxide.

When the acid or acidic gas is added to the sodium silicate, the silica starts precipitating. The acid or acidic gas is added until the sodium oxide of the sodium silicate in the silica is less than about 1 percent by weight. The acid or acidic gas is added to the sodium silicate to neutralize the alkali portion bound to the silicate anion. The reaction slurry is then filtered and washed free of reaction by-product, which is the sodium salt of the acid. The filter cake is dried and milled to obtain a silica of desired degree of fineness.

U.S. Pat. Nos. 3,939,262 and 4,007,260, which issued to Keun Y. Kim, discuss silicas prepared by exchanging hydrogen for the sodium ion of a particulate sodium silicate having an silica/sodium oxide ratio of from 1.6 to 3.75, containing only 10 to 25% by weight of water.

In U.S. Pat. No. 3,838,192, a sodium polysilicate is produced by hydrothermal treatment of a dispersion of silica and sodium hydroxide. After the silicate is partly polymerized, the reaction mixture is spray dried, milled and further processed.

Potassium is a catalyst used in the manufacture of polyols which are used in the manufacture of polyurethane. When the polyol is manufactured, it will be found to contain residual potassium ions. These potassium ions need to be removed before the polyol is used to make flexible polyurethane. Therefore, the polyol manufacturer needs an adsorbent to remove the residual catalyst if he is to guarantee the quality of his polyol.

The characteristics of an adsorbent of this type should be such that it will filter well, have a reasonable absorption capacity, and not leach any impurities into the polyol. The silica of the present invention has these characteristics.

SUMMARY OF THE INVENTION

An object of this invention is to provide an improved adsorbent for polyol purification.

Other objects and a fuller understanding of the invention may be had by referring to the following description and claims.

The present invention achieves its objectives by forming a synthetic amorphous silica in a four step process.

In the first step, an aqueous dispersion including finely divided silica and a sodium hydroxide are subjected to hydrothermal treatment at a temperature and for a period of time effective to react the silica and the sodium hydroxide to form a partly polymerized silicate. The temperature of the hydrothermal treatment is in the range of about 138 to 210 degrees Celsius; is preferably from about 154 to 177 degrees Celsius; and is more preferably about 157 degrees Celsius. The length of the hydrothermal treatment is from about 2.5 to 4.5 hours; and is preferably about 3 hours. The dispersion of silica and hydroxide has a silica/sodium oxide weight ratio of at least 1.8:1; preferably from 2.2:1 to 2.6:1; most preferably about 2.4:1.

In the second step, the reaction mixture is spray dried to form minute hollow spheres of sodium polysilicate having a bulk density of about 0.4 g/cc. The temperature at which the polysilicate is spray dried is at least 204 degrees Celsius; is preferably from about 204 to 538 degrees Celsius; and is most preferably at about 316 degrees Celsius.

In the third step, the polysilicate is reacted with a 5 to 15% sulfuric acid solution, preferably a 11.4% sulfuric acid solution.

In the fourth step, the synthetic silica is filtered, washed and dried.

Any granular amorphous silica would be useful as an adsorbent for polyol purification if it has a BET surface area greater than 60 sq m/g, an oil absorption of between 60 and 140 cc/100 g, and at least 70% of the silica is larger than 44 microns. This adsorbent may also contain up to 5% of a metal cation adduct of either aluminum, magnesium, zinc or calcium.

DESCRIPTION OF THE PREFERRED EMBODIMENTS

In one of its broadest aspects, the present invention is based on the discovery that an adsorbent for polyol purification can be produced by first hydrothermally reacting an aqueous suspension of finely divided silica and an sodium hydroxide to form a reaction mixture of partly polymerized sodium silicate; then spray drying the resulting reaction mixture to form minute hollow spheres of sodium polysilicate; reacting the spray dried polysilicate with sulfuric acid to form a synthetic silica; and then filtering, washing and drying the silica.

In accordance with the present invention, an aqueous dispersion of finely divided silica and a sodium hydroxide are subjected to hydrothermal treatment at a temperature and for a period of time effective to transform the reactants into sodium silicates that are at least partially polymerized and which contains polysilicate ions in a polymerized, irreversible state.

As used herein, the term finely-divided silica refers to a finely divided powder containing at least 99% silica and having a particle size such that at least 95% of the particles are no larger than 75 microns. Silica powders, referred to in the art as "Silica flour" or its equivalent, are suitable.

The hydrothermal treatment of the aqueous dispersion of finely divided silica and hydroxide is effected in a closed vessel at temperatures above the boiling point of the aqueous suspension being treated and under the elevated pressures obtained at such temperatures. Any suitable pressurized equipment may be employed if provided with means for maintaining the aqueous mixture under high agitation and if provided with means (e.g., a steam jacket) for maintaining the dispersion at the desired temperatures and pressures.

In this regard, the hydrothermal treatment of the silica and sodium hydroxide dispersion is conducted at temperatures in the range of from about 138 to 210 degrees Celsius and corresponding pressures of about 5.6 to 21.4 kg/sq cm. A preferred temperature range is from 154 to 177 degrees Celsius and most preferably is 157 degrees Celsius.

The reaction time is a function of the temperature employed. The reaction time must be sufficient to allow the silica and hydroxide to react to form a partly polymerized silicate. Reaction periods on the order of about 2.5 to 4.5 hours are required for the above identified temperature ranges. Higher temperatures result in reduced reaction times but regardless of the temperature, the reaction time must be sufficient to achieve partial polymerization. A preferred reaction time is about 3 hours.

Sodium silicates having a silica to sodium oxide weight ratio on the order of about 1.5:1 are in simple ionic form. As indicated, the first step is directed to a process for making an sodium polysilicate that is at least partially polymerized. Therefore, the concentration of the reactants must be such that the silica/sodium oxide weight ratio of the product is at least 1.8:1. It has been discovered that products having silica/sodium oxide weight ratios of from about 2.2:1 to 2.6:1, preferably 2.4:1, are particularly advantageous. Thus, the initial composition of the reactants (on a dry basis) is from about 69 to 72 percent by weight silica and from about 31 to 28 percent by weight sodium oxide.

The reaction mixture must be fluid. However, very dilute reaction mixtures cause a substantial decrease in the rate of reaction. Preferably, the weight percent of water, based on the total weight of the reaction mixture, is from about 20 to 60%.

In the second step, the reaction mixture is spray dried to form minute hollow spheres of polysilicate having a bulk density of about 0.4 g/cc. The temperature at which the polysilicate is spray dried is at least 204 degrees Celsius, is preferably from 204 to 538 degrees Celsius, and is most preferably at about 316 degrees Celsius.

In the third step, the polysilicate is added to sulfuric acid and allowed to react to form synthetic silica. The concentration of the sulfuric acid solution may vary from 5 to 15%, but it must be sufficient so that essentially all the sodium ions in the sodium silicate are exchanged for hydrogen ions.

The amount of sulfuric acid solution used must be large enough relative to the amount of sodium silicate to insure that essentially all sodium ions in the solid phase are replaced by hydrogen ions. The use of large amounts of sulfuric acid solution is of no particular advantage and is avoided for reasons of economy. A convenient method for controlling the ratio of acid to silicate is by pH measurement in the reactor. The optimum final pH is from about 2 to about 7.

Adequate reaction time must be provided to allow the exchange of hydrogen ions for sodium ions to go substantially to completion. Completion of the reaction can be recognized by observing the cessation of reaction mixture pH drift. A preferred reaction time is about 1 hour. This reaction may be carried out at any convenient temperature, for example, from about 15 to about 80 degrees Celsius.

In the fourth step the silica is filtered, washed and dried. Because of the granular nature of the starting sodium silicate particles, and because these particles do not appreciably disintegrate during ion exchange, the amorphous silica thus formed can be readily separated from the mother liquor using a filter and washed without difficulty. The silica thus separated does not contain much water and, therefore, requires less drying. The amorphous silica formed is dried in any conventional dryer.

In the most preferred embodiment, sodium hydroxide in the form of a concentrated solution preferably containing about 50% NaOH is charged to an agitated reaction vessel. Thereafter finely divided silica, which is introduced as an aqueous slurry, is charged to the reaction vessel. The dispersion of silica and sodium hydroxide has an silica/sodium oxide weight ratio of from about 2.4:1. The aqueous dispersion is kept under constant agitation during the charging as well as during the reaction period. The concentrated caustic solution is preferably preheated to a reaction temperature of 157 degrees Celsius prior to the introduction of the silica slurry. If the caustic solution is not preheated, the aqueous solution containing the silica and hydroxide is initially heated to the reaction temperature. The reaction mixture is maintained at the reaction temperature for about 3 hours.

At the end of the reaction period, the reaction vessel is vented and the mixture is passed by gravity, into a drop tank which contains dilution water at approximately ambient temperatures. In this manner, the temperature of the reaction mixture is cooled quickly and efficiently and the weight ratio of the reaction product to water is adjusted to the concentration required for the spray drying of the product.

The aqueous mixture in the drop tank is passed through a clarification filter to remove small quantities of insolubles, such as sand, unreacted silica and the like. The clarified aqueous mixture may then be passed into a hold or storage tank or fed directly into the upper portion of a spray dryer.

The aqueous mixture is introduced into the upper portion of the generally upright, cylindrical chamber of the spray dryer and passes through a spray nozzle. The latter causes the aqueous mixture to be finely and evenly dispersed within the chamber and in direct contact with a mass of upwardly directed hot air. Suitable control valves may be provided for regulating the rate of feed of the reaction mixture, as well as that of upwardly directed air. The spray drying is effected at about 316 degrees Celsius. In a preferred range of spray drying, inlet air temperatures are on the order of from about 204 to 538 degrees Calsius. In this manner, the "flashing off" of the water in the spray dryer is effected rapidly with the resultant spray dried droplets being in the form of hollow microspheres having a bulk density of about 0.4 g/cc.

The sodium polysilicate is then reacted with an 11.4% solution of sulfuric acid solution for sufficient time to replace the sodium ions in the particulate sodium polysilicate with hydrogen ions. The concentration is preferably on the order of 11.4% but other concentrations can be used. The reaction is continued until all of the sodium ions have been replaced. Once the synthetic amorphous silica is produced, it is filtered, washed and dried.

Silicas with a BET surface area greater than 60 sq m/g; an oil absorption of between 60 and 140 cc/100 g; and at least 70% of the silica particles larger than 44 microns are particularly useful as adsorbents for polyol purification.

The characteristics of a good adsorbent for polyol purification are: (1) it should filter well; (2) it should have a reasonable adsorption capacity; and, (3) it should not leach any impurities into the polyol.

Silicas which have at least 70% of the particles larger than 44 microns are so coarse as to filter exceptionally well.

Silicas having an oil absorption of between 60 and 140 cc/100 g, have a reasonable adsorption capacity.

Silicas, being basically pure silica, have no impurities to leach into the polyol.

These silicas can be made as described by hydrothermally reacting, under certain controlled conditions, an aqueous suspension of finely divided silica and an alkali metal hydroxide to form a partly polymerized silicate; spray drying the resulting reaction mixture to form spheres of sodium polysilicate; reacting the polysilicate with an acidic solution to form a synthetic silica; and then filtering, washing and drying the silica.

Other silicas having an oil absorption of between 60 and 140 cc/100 g; a BET surface area greater than 60 sq m/g; and at least 70% of the silica larger than 44 microns can be produced by the processes disclosed in U.S. Pat. Nos. 3,893,840; 3,998,162; and 3,960,586. The disclosure of these three patents are hereby incorporated by reference.

When up to 5% of a metal cation adduct, such as aluminum, magnesium, zinc, or calcium is added to any of the adsorbents above, there is a significant improvement in surface area.

The invention will be further illustrated by the following examples which set forth particularly advantageous method and composition embodiments. While the examples are provided to illustrate the present invention, they are not intended to limit it thereto.

PREPARATION OF SODIUM POLYSILICATE

EXAMPLE A

A hollow, spherical sodium polysilicate was prepared by the following process. 4,024 kg of a 50% NaOH solution was charged to a stainless steel autoclave provided with means for continuously agitating the solution. A silica slurry, prepared by dispersing 4,204 kg of silica flour into 2,292 kg of water, was then charged to the reactor. The autoclave was sealed and the temperature of the aqueous mixture was preheated (by the introduction of steam into an exterior steam jacket) to 157 degrees Celsius over a one-hour period producing a pressure of 8.1 kg/sq cm. The reaction mixture was thereafter maintained at this temperature for 3 hours. Continuous agitation was maintained throughout the heat-up and reaction period. At the end of the three-hour reaction cycle, the steam was shut off and the autoclave partially vented to reduce the pressure to about 5.3 kg/sq cm. The vent was then fully opened and the reaction mixture fed by gravity into a drop tank positioned beneath the autoclave and containing 6,869 kg of water at 25 degrees Celsius. The mixture in the drop tank was pumped through a classification filter and introduced into the upper portion of a spray dryer.

The aqueous mixture was fed into the spray dryer at a rate of 9,571 kg per hour, the concentration of the mixture comprising 0.48 kg of sodium polysilicate per liter. The speed of the spray nozzle was about 11,000 rpm. The spray dryer inlet and outlet air temperatures were 316 and 93 degrees Celsius, respectively. The spray dried product was collected and withdrawn from the base of the spray dryer by a screw conveyor. 5,661 kg of sodium polysilicate, having a silica/sodium oxide weight ratio of 2.4:1 and a density of 0.128 g/cc was recovered from the spray dryer. The fact that the product produced in this example was partially polymerized was established by conductivity tests as determined by the Harman technique, set forth in R. W. Harman, *Journal of Physical Chemistry* 32, 44–60 (1928).

EXAMPLE B

The procedure of Example A was repeated except that the temperatures and pressures of the hydrothermal reaction were varied in a series of examples as shown by the following table.

TABLE I

| Run No. | Temperature (Celsius) | Pressure kg/sq cm | Reaction time (min.) |
|---|---|---|---|
| 1 | 127 | 4.5 | 270 |
| 2 | 138 | 5.5 | 240 |
| 3 | 160 | 8.3 | 180 |
| 4 | 177 | 11.5 | 175 |
| 5 | 193 | 15.8 | 160 |
| 6 | 210 | 21.4 | 150 |

The products obtained in these runs were the same as that obtained in Example A. From the Table, it may be seen that an increase in the temperature and pressure increases the rate of the hydrothermal synthesis.

Further, it was noted that hydrothermal reactions conducted at temperatures below 127 degrees Celsius produced little polysilicate transformation even for reaction periods on the order of 10 hours or longer.

EXAMPLE C

In a series of tests, the procedures of Example A were repeated except that the quantities of reactants in the hydrothermal treatment were varied as indicated.

TABLE II

| Run No. | Reactants, wt. percent | | | Product silica/sodium oxide wt. ratio obtained |
|---|---|---|---|---|
| | silica | NaOH | water | |
| 1 | 39.0 | 21.6 | 39.4 | 2.3 |
| 2 | 42.5 | 17.7 | 39.8 | 2.5 |
| 3 | 43.4 | 16.6 | 40.0 | 2.6 |
| 4 | 43.8 | 16.2 | 40.0 | 2.7 |

PREPARATION OF SILICAS

EXAMPLE I 1045 g of a sodium polysilicate similar to that of Example A but having a bulk density of 0.416 g/cc was added to 3000 ml of 11.4% sulfuric acid in 40 minutes. The reaction slurry (pH of 4.0) was filtered in a Buchner filter. The wet cake was washed with tap water and dried at 150 degrees Celsius. Pertinent data is set forth in Table III.

EXAMPLE II

The procedures of Example I were repeated except that: (1) 525 g of sodium polysilicate was added to 3000 ml of 5.7% sulfuric acid in 50 minutes; and (2) the final pH of the reaction slurry was 6.0. Results of the experiment are listed in Table III.

TABLE III
UNMILLED SILICA

| EXAMPLE | I | II |
|---|---|---|
| Sulfuric acid, % | 11.4 | 5.7 |
| Density, g/cc | 0.416 | 0.416 |
| Final pH, reaction | 4.0 | 6.0 |
| Reaction time, min. | 40.0 | 50.0 |
| % Wet Cake Moisture | 70.5 | 80.0 |
| BET Surface Area, sq m/g | 436.0 | 281.0 |
| Oil Absorption, cc/100g | 68.0 | 73.0 |

The adsorption capacity of silica adsorbent for the alkaline component (residual catalyst) in polyol was determined by first preparing a polyol solution containing 0.3% potassium hydroxide (KOH). The adsorbent was mixed with the polyol—KOH solution and after a specified length of time the polyol was filtered. the residual concentration of KOH in the filtrate was determined by atomic absorption (AA) spectroscopy.

In the actual test method a 3-neck flask was used and fitted with an agitator and thermometer. 200 grams of crude polyol containing 0.3% KOH was added to the 3-neck flask. The polyol solution was heated to 95 degrees Celsius and then 2 grams of synthetic silica absorbent was added. The adsorbent polyol mixture was heated for 40 minutes and then filtered immediately into a 7 centimeter diameter Buchner funnel using a No. 1 Whatman filter paper. The filtrate was analyzed for residual KOH. The following data was obtained (see Table IV).

TABLE IV

| Silica Adsorbent | % Residual KOH in Filtrate | Silica Adsorption Capacity mg KOH/g |
|---|---|---|
| From Example I | 0.10 | 200 |
| From Example II | 0.08 | 220 |

From data in Table IV, it is clear that synthetic silicas of the present invention can be efficiently used to remove traces of alkaline catalyst impurities such as KOH from polyols.

EXAMPLE III 114 liters of a 0.15 kg/liter sodium silicate solution (silica to sodium oxide molar ratio of 2.5) was added to a stirred reactor and the silicate solution was heated to 85 degrees Celsius. Sulfuric acid of 11.2 percent concentration was added to the reactor at the rate of 3.07 liters per minute until a pH of 10.0, plus or minus 0.1, was reached. At this pH, the precipitation of silica micelles just started. The acid was shut off and the reaction medium was aged for 10 minutes. After the aging period, both acid and silicate were added simultaneously at the rate of 3.18 and 3.79 liters per minute, respectively. The silicate was turned off after 30 minutes, the acid addition was continued and the batch was finished off at pH 5.8, then filtered, washed and dried.

The percent wet cake moisture was 65%; the BET surface area was 66 sq m/g; the oil absorption was 85 cc/100 g; and at least 70% of the particles were larger than 44 microns.

EXAMPLE IV

Dry sodium sulfate was added to 37.9 liters of water in a 757 liter reactor such that the sodium sulfate concentration in the reaction medium was 10%. The pH of the reaction medium was adjusted to 9.0 by the addition of sodium silicate. The reaction medium was then heated to 66 degrees Celsius. Sodium silicate having a silica and sodium oxide mol ratio of 2.5 and a concentration of 0.24 kg/liter and sulfuric acid of 11.4% concentration were then added to the reaction medium at the rate of 756 ml/min and 453 ml/min respectively so that a constant precipitation pH of 9.0 was maintained. The sodium silicate solution employed in this Example also contained 7% sodium sulfate which was added to the solution prior to its introduction into the reactor. After 30 minutes, the precipitation was complete. Excess acid was adde until a slurry pH of 5.4 was reached. The reaction slurry was digested at 77 degrees Celsius for 20 minutes and then filtered, washed and dried.

The product had a wet cake moisture content of 51%; and a BET surface area of 173 sq m/g; and at least 70% of the particles were larger than 44 microns.

Thus, in operation, a granular amorphous silica is useful as an adsorbent for polyol purification if it has a BET surface area greater than 60 sq m/g; an oil adsorption of between 60 and 140 cc/100 g; and at least 70% of the particles are larger than 44 microns. This silica can be produced either by the reacting of a dried polysilicate with acid or by reacting acid with an aqueous dispersion of silicate. Up to 5% of a metal action adduct such as aluminum, magnesium, zinc or calcium can be added to the silica to increase surface area.

While the present invention has been described with reference to specific embodiments, this application is intended to cover those various changes and substitutions which may be made by those skilled in the art without departing from the spirit and scope of the appended claims.

I claim:

1. A method of producing an adsorbent for polyol purification comprising a synthetic amorphous silica having at least 70% of the silica larger than 44 microns produced by the method comprising the steps of:

divided silica and an sodium hydroxide to hydrothermal treatment at a temperature in the range from about 138 to 210 degrees Celsius and for a period of time of from about 2.5 to 4.5 hours and sufficient to react the silica and said sodium hydroxide to form a reaction mixture of partly polymerized sodium silicate, said aqueous dispersion having a silica/sodium oxide weight ratio of at least 1.8:1;

(b) spray-drying said reaction mixture at a temperature of at least 204 degrees Celsius to form minute hollow spheres of sodium polysilicate having a bulk density of about 0.4 g/cc;

(c) reacting the polysilicate with a 5 to 15% sulfuric acid solution to form a synthetic amorphous silica; and (d) filtering, washing and drying the synthetic amorphous silica.

2. A method of producing an adsorbent according to claim 1 wherein a metal cation adduct selected from the group consisting of aluminum, magnesium, zinc and calcium is added to said synthetic silica until the silica contains up to 5% by weight of said metal cation adduct.

* * * * *

UNITED STATES PATENT AND TRADEMARK OFFICE
CERTIFICATE OF CORRECTION

PATENT NO. : 4,296,000
DATED : October 20, 1981
INVENTOR(S) : Satish K. Wason

It is certified that error appears in the above—identified patent and that said Letters Patent is hereby corrected as shown below:

Column 3, line 47, preceding "sodium", "an" should be -- a --.

Column 4, line 40, preceding "silica/sodium", "an" should be -- a --.

Column 5, line 8, "Calsius" should be -- Celsius --.

Column 8, line 40, "adde" should be -- added --.

Column 8, Claim 1, after line 67 and preceding line 68, add:
 -- (a) subjecting an aqueous dispersion including finely --.

Column 8, Claim 1, line 68, preceding "sodium", "an" should be -- a --.

Signed and Sealed this

Second Day of March 1982

[SEAL]

Attest:

GERALD J. MOSSINGHOFF

Attesting Officer   Commissioner of Patents and Trademarks